United States Patent [19]

Kadel

[11] Patent Number: 5,133,457
[45] Date of Patent: Jul. 28, 1992

[54] TAMPON ASSEMBLY, INCLUDING WRAP FOR DISPOSAL OF SPENT APPLICATOR

[75] Inventor: Betty Kadel, Allendale, N.J.

[73] Assignee: Playtex Family Products Corporation, Stamford, Conn.

[21] Appl. No.: 718,520

[22] Filed: Jun. 21, 1991

[51] Int. Cl.⁵ .......................... B65D 5/54; B65D 83/02
[52] U.S. Cl. ...................................... 206/438; 206/37; 229/87.05
[58] Field of Search ............... 206/438, 440, 441, 610, 206/620, 621, 604, 627, 37, 38, 496; 229/87.05

[56] References Cited

U.S. PATENT DOCUMENTS

| | | | |
|---|---|---|---|
| 2,478,412 | 8/1949 | McMahan | 206/440 X |
| 2,587,515 | 2/1952 | Parish | 206/438 X |
| 2,587,717 | 3/1952 | Fourness | 206/438 X |
| 2,720,881 | 10/1955 | Jones | 206/363 X |
| 3,092,251 | 6/1963 | Jaggers | 206/438 X |
| 3,193,181 | 7/1965 | Konjevich e al. | 206/496 X |
| 4,027,670 | 6/1977 | Bronner | 206/438 X |
| 4,648,513 | 3/1987 | Newman | 206/627 X |
| 4,881,644 | 11/1989 | Norquest et al. | 206/627 X |

Primary Examiner—Paul T. Sewell
Assistant Examiner—Jacob K. Ackun, Jr.
Attorney, Agent, or Firm—Stewart J. Fried

[57] ABSTRACT

A tampon applicator assembly is disclosed wherein the protective wrap which initially packages the tampon applicator provides a simplified covering for disposal of the spent applicator. The tampon applicator wrap is opened at a pre-determined location such that a discrete portion remains which is significantly longer than the applicator barrel member. Accordingly, after tampon ejection, with the plunger telescopingly located within the barrel, that unit is then inserted within the discrete wrap portion, which includes a substantial length extending beyond the reinserted applicator. That substantial length is then twisted and tucked into the opened end of the applicator to maintain closure of the wrap for applicator disposal.

7 Claims, 1 Drawing Sheet

TAMPON ASSEMBLY, INCLUDING WRAP FOR DISPOSAL OF SPENT APPLICATOR

FIELD OF THE INVENTION

The present invention relates to tampon assemblies, and more particularly, to such an assembly in which the protective wrap provides a means for the sanitary and discreet disposal of the spent applicator in a simplified manner.

DESCRIPTION OF THE RELATED ART

Sanitary protection products, such as tampons and sanitary napkins, are generally commercially available with individual protective wraps. To use the typical tampon, the wrap is opened, the tampon is removed from the wrap and inserted then within the body. For ease of insertion, the substantial majority of tampons are dispensed in individual telescoping type applicators. The applicators generally include a barrel member which initially contains the tampon for ejection from one end of the barrel, and a plunger which is inserted within the opposite end of the barrel. The plunger is then pushed against the tampon, in a telescoping manner, for ejection of the tampon from the barrel member. The user must then discard the spent individual applicator. For purposes of discreet and sanitary disposal, it is desirable that the applicator be wrapped prior to discarding.

Newman U.S. Pat. NO. 4,648,513 is generally directed to such disposal by providing a specially designed package including a supplemental panel with an adhesive strip to reseal the package after the tampon or sanitary napkin has been removed. The package is made from a sheet of material which has a pair of perforation lines that form tear lines at both ends of the wrap, past the enclosed sanitary protection product. A supplemental flap is then provided to adhesively reseal the package after the used sanitary protection product is placed therein. The addition of the flap and adhesive material adds to the cost of the packaging. Further, the need for a pair of tear lines to be beyond both ends of the enclosed product increases the amount of wrap material, making the wrap even more costly, and lengthens the size of the overall package assembly.

Harvey U.S. Pat. No. 3,276,670 and Konjevich et al U.S. Pat. No. 3,193,181 disclose disposable wrappers for a sanitary napkin which, after reinserting the used sanitary napkin in the opened wrap, require the open end of the wrap to be tied into a knot prior to disposal of the used napkin. Pickens U.S. Pat. No. 2,750,033 and McMahan U.S. Pat. No. 2,478,412 disclose sanitary napkin packages which are thereafter rolled to enclose the soiled napkin.

The various prior art packages for disposing of the soiled sanitary protection product have not been commercially feasible in that they all require a significant revision to the packaging, which adds to the cost or is otherwise impractical. This is exemplified by the 1) addition of another panel and the adhesive strip of Newman U.S. Pat. No. 4,648,513; the additional packaging material and substantial user dexterity required by the knot tying arrangement of Harvey U.S. Pat. No. 3,276,670 and Konjevich et al U.S. Pat. No. 3,193,181,and 2) semirigid packaging materials required to maintain the rolled closure of Pickens U.S. Pat. No. 2,750,003 and McMahan U.S. Pat. No. 2,478,412.

SUMMARY OF THE INVENTION

The present invention is generally directed to providing a simple seal for the spent tampon applicator which is cost effective, and requires a minimal change with respect to existing products. It may easily be used for the efficient and effective disposal of the spent applicator. Specifically, the disposal system of the present invention may be achieved by virtue of a very slight modification to existing type packaging presently being utilized for the mass production of commercial tampon assemblies. Such packages are formed from a flaccid material, such as a voided polypropylene film. Alternatively, a low density polyethylene film or paper may be used. A separating means, such as a horizontal score line, is located along the length of the package to readily facilitate the user's separation of the package into two discrete sections, so as to expose the tampon assembly contained therein. The score line is placed at a predetermined position to enable the user to remove the tampon without touching the insertion end. The score line has generally been placed close to the fingergrip region of the barrel member. In accordance with the present invention, the score line is displaced outward, beyond the underlying barrel member. Accordingly, after opening the wrapper, that portion of the wrapper containing the barrel will include a freely extending length which projects significantly beyond the finger grip end of the barrel.

After removal of the applicator from within the wrap, and the telescoping ejection of the tampon from the barrel member, the barrel member (with the plunger disposed therein) is then reinserted within the elongated portion of the wrap. By virtue of the wrapper separating means having been predeterminedly located beyond the length of the barrel member, there will now be a significant length of freely extending wrap. That freely extending wrap is then used to enclose the spent barrel within the wrap by first twisting it, at least 180 degrees, and then tucking the free end within the opened end of the barrel. This has been found to provide a sufficiently effective closure to maintain the spent applicator within the applicator wrap for discreet and sanitary disposal thereof, without the need to use adhesives, additional sealing flaps or stiffened wrapper materials.

It is primary object of the present invention to provide a tampon package assembly in which the protective wrap provides an improved means for discarding the spent applicator.

It is another object of the present invention to provide such a tampon package assembly which requires only a minimal modification with respect to existing commercial protective wraps.

It is still another object of the present invention to provide such a tampon assembly wherein the disposing of the spent applicator includes the steps of placing it within the previously opened wrap, and simply twisting the free end of the wrap and tucking same into the open end of the tampon barrel.

It is yet another object of the invention to provide a method of packaging, dispensing and disposing of a tampon assembly wherein the tampon wrap is separated into two discreet portions, with one of the portions having a free end such that when the spent applicator is thereafter inserted within that wrapped portion, the free end may be simply twisted and tucked into the contained barrel for sanitary disposal of the spent applicator.

To accomplish the forgoing objects and advantages of the present invention, the tampon package assembly includes a telescoping type tampon applicator having a barrel member and plunger. The applicator is initially enclosed within a protective wrap formed of a flaccid material. The wrap is separated at a predetermined position along its length to obtain access to the enclosed applicator. The line of separation is axially beyond the finger grip end of the barrel member, such that when the wrap is opened the remaining wrap portion has a significant length extending beyond the finger grip end of the barrel member. When the barrel member is reinserted within that wrapped portion, the free end is of a sufficient length to readily permit twisting and tucking within the opened end of the barrel to maintain the wrap closure about the spent barrel.

BRIEF DESCRIPTION OF THE DRAWINGS

The foregoing will be more apparent from the following detailed explanation of a preferred embodiment of the invention in connection with the accompanying drawings wherein.

Figure 1:
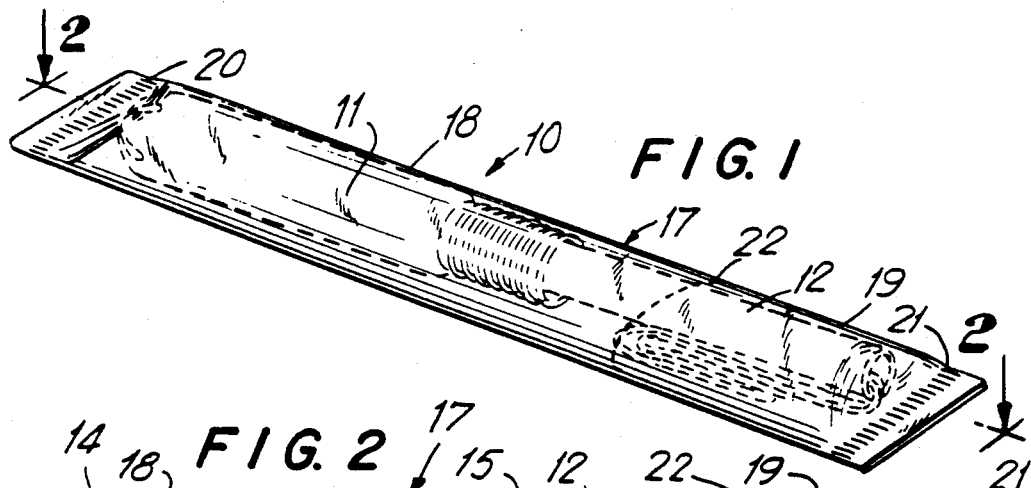
FIG. 1 is a perspective view of the tampon package assembly prior to opening.
Figure 2:
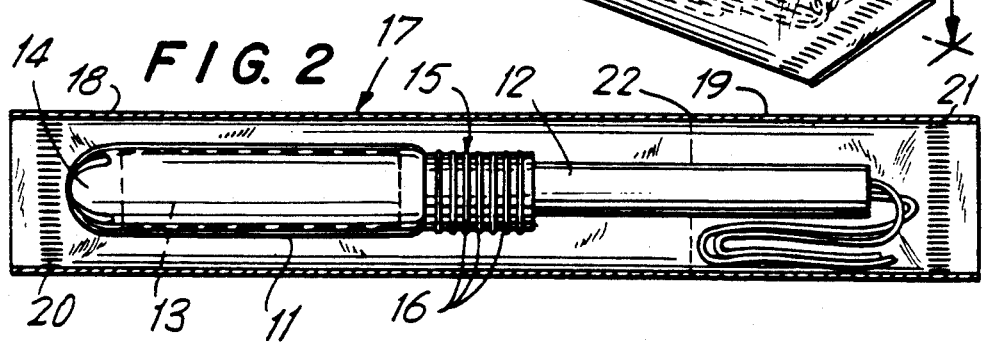
FIG. 2 is a side view of the tampon package assembly of FIG. 1, along the line 2—2.

Referring to the drawings and initially to FIGS. 1 and 2, there is disclosed a tampon package assembly 10 which includes a well known type of telescoping tampon applicator comprising barrel members 11 and plunger 12. Barrel member 11 contains tampon 13. The applicator shown preferably includes a rounded tip 14 having a plurality of petals, and may generally be of the type which is the subject of assignee's Berger, et al. U.S. Pat. No. 3,895,634. It should, however, be understood that other types of tampon applicators may be used in conjunction with the present invention, including cardboard applicators and those that do not have a rounded tip, as well as compact type applicators, in which the plunger is initially contained within the barrel, such as are the subject of assignee's Melvin, et al. U.S. Pat. No. 4,891,042 and Stewart et al. U.S. Pat. No. 4,911,687, or Ring U.S. Pat. No. 4,286,595. In all of said applicators, the plunger 12 is urged against the rear of tampon 13 to eject the tampon through ejection end 14 of the barrel member. The barrel member also preferably includes a finger grip region 15 at its opposite end which may include a series of ridges 16 to facilitate the user's grasping of the applicator within her hand.

The applicator assembly is initially protectively packaged within a wrap 17. Wrap 17 which is a flaccid material, may preferably be formed of a voided polypropylene film, with its ends sealed at 20 and 21, as is the subject of assignee's Ingersoll, et al. U.S. Pat. No. 4,617,781. As disclosed therein, the voided polypropylene film may be of the type which is sold by Hercules Incorporated as their type WT 503 film (Hercules is a registered trademark of Hercules Incorporated). Alternatively, other flaccid material wraps may be used such as low density polyethylene, a paper, (including suitably coated paper).

A wrap separating means, such as a series of horizontally disposed and spaced score lines 22, are placed along the protective wrap 17 to facilitate the user's opening of the wrap and separation thereof into two discrete portions—18, 19. Typically, the user will hold the opposite ends of the tampon assembly in her two hands, and pull the extreme end of wrap 19 to open the wrap along score lines 22. When so opened, the barrel, including its ejection end 14 will be retained within the protective wrap section 18 to protect end 14 against handling, and possible soiling prior to placement within the body. The tampon applicator assembly is then removed from the wrap, and plunger 12 is telescoped into barrel 11, against the rear end of the tampon 13 to eject the tampon for insertion into the body in the conventional matter.

Figure 5:
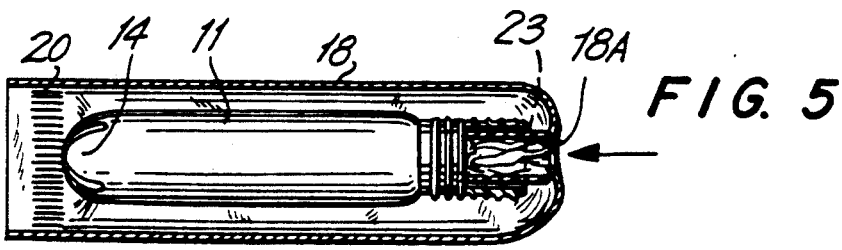
FIG. 5 is a side view showing the final step of enclosing the spent applicator within the wrapper portion, with the assembly now being in condition for sanitary discarding of the spent applicator.

In accordance with the present invention, the spent applicator, with the plunger 12 telescopingly contained within barrel 11 is then reinserted within discreet wrapper portion 18, as shown in FIG. 2. Of particular importance, due to the location of separating means 22, there is a freely extending portion 18A of the wrap which axially extends beyond the barrel member when it is reinserted within wrapper portion 18. In accordance with the present invention, this freely extending portion 18A is then twisted, preferably at least about 180 degrees to the condition shown in FIG. 3. Thereafter, the freely extended portion is then tucked into the end 23 of the spent applicator assembly contained within wrapper portion 18, to the final condition shown in FIG. 5. It has been determined that the twist and tuck simplified technique provided by the instant invention provides a sufficient closure of the wrap about the spent applicator to provide a sanitary containment for applicator disposal.

Figure 3:
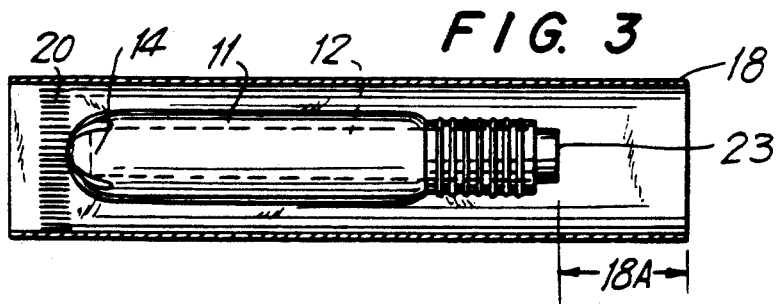
FIG. 3 is a side view, corresponding to FIG. 2, after removal of the applicator, ejection of the tampon from the barrel, and reinsertion of the spent applicator within a portion of the wrap.
Figure 4:
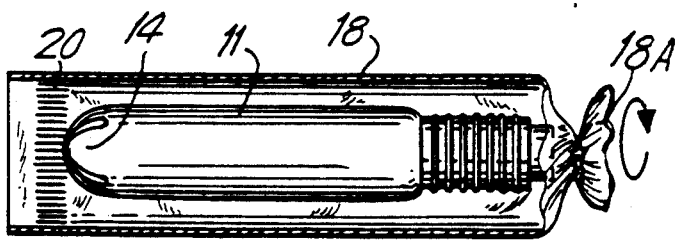
FIG. 4. is a side view showing the next step for closing the wrap with the spent applicator therein.

In accordance with a preferred embodiment of the present invention, the applicator assembly, including barrel 11 and plunger 12 is, in the condition shown in FIG. 2, approximately 4¾ inches in length, with the barrel as shown by dimension B in FIG. 3 being approximately 2¾ inches. The separating means 22 in this embodiment is predetermingly positioned such that the discrete wrapper portions are in the order of 4 inches and 1 inch respectively. Accordingly, when the spent applicator is thereafter inserted within wrap portion 18 (as shown in FIG. 3) the freely extending portion 18A of the wrap will be in the order of 1 inch. It should however be understood that these dimensions are only given for illustrative purposes, and the invention may be practiced in conjunction with other tampon applicator assemblies.

Having thus described the invention with particular reference to the preferred form thereof, it would be obvious that various changes and modifications may be made therein without departing from the spirit and scope of the invention as defined by the appended claims.

What is claimed is:

1. A tampon package assembly comprising: a tampon applicator having a barrel member for containing a tampon therein and a plunger member for reciprocal movement within said barrel member to eject the tampon from said barrel member, said barrel member having a fingergrip region at one end which includes means to facilitate manual grasping of said one end region of the barrel and a tampon ejection end at its opposite end; and a protective wrapper formed of a flaccid material, having a hollow body for initially containing said tampon applicator therein, wrapper separating means located at a predetermined position along said wrapper to separate said wrapper into first and second discrete portions prior to removing the tampon applicator from the protective wrapper;

said second wrapper portion including opposed first and second ends, said first end located at said separating means and means sealing said second end;

said tampon ejection end of the applicator initially located at said sealed second end;

said separating means extending transverse to the sealed applicator members contained therein, at a location axially beyond the fingergrip end of the barrel member contained therein, in a direction opposite the tampon ejection end, such that said second discrete wrapper portion is significantly longer than said barrel member and includes a freely extending length which covers and projects significantly beyond said fingergrip region;

the freely extending portion of said second wrapper portion which extends beyond the fingergrip end of said barrel member providing a subsequent wrapper closure means for disposal of the spend applicator within said second discrete wrapper portion with the plunger member telescopingly contained within said barrel member which is devoid of the tampon;

said wrapper closure means adapted to be twisted about a section intermediate its second end and the fingergrip end of the barrel member reinserted therein, and thereafter tucked within the open fingergrip end of the barrel member, to reclose said first end of the second wrapper portion and said wrapper closure means maintaining the enclosure of the spent applicator within said second wrapper portion.

2. A tampon package assembly as set forth in claim 1, wherein said wrapper is formed of a voided polypropylene film.

3. A tampon assembly as set forth in claim 1, wherein said wrapper is formed of a low density polyethylene film.

4. A tampon assembly as set forth in claim 1, wherein said wrapper is formed of paper.

5. A tampon assembly as set forth in claim 1, wherein said barrel member is in the order of 2¾ inches, and said second discrete portion between said wrapper first end and sealing means is in the order of 3¾ inches.

6. A tampon assembly as set forth in claim 1, wherein the closure means portion of said second wrapper portion is in the order of one inch.

7. The tampon assembly of claim 1, wherein the wrapper separating means is formed of a perforate line extending across the wrapper at said predetermined position.

* * * * *